United States Patent
Ilmola et al.

(10) Patent No.: US 9,970,919 B2
(45) Date of Patent: May 15, 2018

(54) METHOD AND DEVICE FOR MONITORING AND CONTROLLING THE STATE OF A PROCESS STREAM

(71) Applicant: Kemira Oyj, Helsinki (FI)

(72) Inventors: Pekka Ilmola, Oulu (FI); Kaj Jansson, Tampere (FI); Iiris Joensuu, Espoo (FI); Marjatta Piironen, Espoo (FI)

(73) Assignee: KEMIRA OYJ, Helsinki (FI)

( * ) Notice: Subject to any disclaimer, the term of this patent is extended or adjusted under 35 U.S.C. 154(b) by 712 days.

(21) Appl. No.: 14/362,135

(22) PCT Filed: Nov. 30, 2012

(86) PCT No.: PCT/FI2012/051190
§ 371 (c)(1),
(2) Date: Jun. 2, 2014

(87) PCT Pub. No.: WO2013/079801
PCT Pub. Date: Jun. 6, 2013

(65) Prior Publication Data
US 2014/0343872 A1    Nov. 20, 2014

Related U.S. Application Data

(60) Provisional application No. 61/566,023, filed on Dec. 2, 2011.

(30) Foreign Application Priority Data

Dec. 2, 2011    (FI) ...................................... 20116227

(51) Int. Cl.
*G01N 33/18*    (2006.01)
*G01N 33/487*    (2006.01)
*G01N 33/34*    (2006.01)

(52) U.S. Cl.
CPC ...... *G01N 33/1826* (2013.01); *G01N 33/1806* (2013.01); *G01N 33/343* (2013.01); *G01N 33/48735* (2013.01)

(58) Field of Classification Search
CPC ............ G01N 33/1826; G01N 33/343; G01N 33/48735; G01N 33/1806
See application file for complete search history.

(56) References Cited

U.S. PATENT DOCUMENTS

| 3,731,522 A | 5/1973 | Mikesell |
| 4,073,692 A | 2/1978 | Ciaccio et al. |

(Continued)

FOREIGN PATENT DOCUMENTS

| DE | 20001351 U1 | 5/2000 |
| DE | 102004048316 A1 | 4/2006 |

(Continued)

OTHER PUBLICATIONS

Norris et al., Methods in Microbiology, Academic Press, London, 1970, pp. 104.*

(Continued)

*Primary Examiner* — Mohamed Charioui
*Assistant Examiner* — Catherine Rastovski
(74) *Attorney, Agent, or Firm* — Birch, Stewart, Kolasch & Birch, LLP

(57) ABSTRACT

The present invention concerns a method of estimating and optionally controlling the microbiological state in a process stream of an industrial process by measuring the concentration of dissolved oxygen or the rH value, or both, in said stream, the method including continuous or periodic sampling and online measurement. The invention also concerns a device suitable for use in implementing said method.

16 Claims, 8 Drawing Sheets

(56) References Cited

U.S. PATENT DOCUMENTS

| | | | |
|---|---|---|---|
| 2001/0051354 A1 | 12/2001 | Monget et al. | |
| 2008/0199901 A1* | 8/2008 | Enzien | C12Q 1/04 435/29 |
| 2009/0206033 A1* | 8/2009 | Kojima | C02F 3/12 210/623 |
| 2012/0142115 A1* | 6/2012 | Banks | G01N 21/643 436/84 |
| 2013/0015137 A1* | 1/2013 | Urmenyi | B01D 37/041 210/654 |

FOREIGN PATENT DOCUMENTS

| | | |
|---|---|---|
| DE | 102009007851 A1 | 8/2010 |
| GB | 2184110 A | 6/1987 |
| JP | 2007289004 A | 11/2007 |
| NL | 1026287 C2 | 11/2005 |
| WO | WO9726525 A1 | 7/1997 |
| WO | WO9815645 A1 | 4/1998 |
| WO | WO2005022278 A1 | 3/2005 |
| WO | WO2008101089 A2 | 8/2006 |
| WO | WO2009067514 A1 | 5/2009 |

OTHER PUBLICATIONS

Bachmann et al.: "Investingating and modeling the development of septic sewage in filed sewers under static confitions: A lab-scale feasibility study", Science of the Total Environment, Elseviser, Amsterdam, NL, vol. 388, No. 1-3, Oct. 17, 2007.

\* cited by examiner

METHOD AND DEVICE FOR MONITORING AND CONTROLLING THE STATE OF A PROCESS STREAM

BACKGROUND OF THE INVENTION

Field of the Invention

The present invention concerns a method and device for monitoring and optionally controlling the microbiological state in process streams based on the measurement of variables, such as dissolved oxygen or rH or both, optionally assisted by soft sensors, based e.g. on Linguistic Equations (LE).

Description of the Related Art

A common problem in many industrial process systems, e.g. in paper and pulp processing systems, is microbial growth, if microbes are not controlled efficiently. Microbiological growth may cause several problems in the systems. The bacteria in a process stream may cause spoilage of the stream or bacteria may attach to system surfaces forming biofilm or slime. For example, biofilm masses that detach from system surfaces can be carried into the pulp waters and formed into the paper sheet thereby weakening the formed paper sheet quality, e.g. by causing it to tear or causing holes in the paper.

Industrial processes, such as the paper or board manufacturing process, often contain process stages where the process streams are kept in tanks for longer periods of time. These process stages are ideal for the development of microbes, whereby there may be an increase in the microbial content of said streams. Other examples of locations ideal for microbiological growth in a process system are dead zones of process systems (e.g. poor mixing zones).

In the industrial process systems, e.g. in manufacturing of paper or board, microbe analyses are presently carried out in the laboratory due to the lack of fast online measuring methods and devices. The methods, e.g. plate count, are time-consuming and it can take up to 2-3 days to get the results of the analysis. Further, as there always exist a delay between the laboratory analysis results and the changes in the process conditions, the result may be an inadequate biocide dosage to the process stream and, thus, a poor paper quality as well as a poor cost-efficiency of the process. The same is true for other processes requiring biocides to maintain a low level of microbes in a process stream.

WO 2008/101089 describes a method of monitoring microbiological activity under aerobic conditions in process streams based on changes on dissolved oxygen concentrations measured using specified process steps. However, the measurement is claimed not to be suitable for process streams of low dissolved oxygen concentration. Further, the process is complex, requiring cleaning of the measuring probes between measurement points during measurement cycles.

Further, there is not available a method for reliably monitoring microbiological state under anaerobic conditions in process streams.

Thus, there is a need for simpler measurement methods to monitor the microbiological state of process streams, in particular on-line, and optionally to control microbiological state of process streams e.g. by controlling the effective amounts of biocide(s) to be added to the processes to maintain an acceptable microbiological state in said streams. In addition, there is a need to be able to monitor the microbiological state also at low dissolved oxygen concentrations in process streams, and in anaerobic conditions.

SUMMARY OF THE INVENTION

It is an aim of the present invention to eliminate at least a part of the problems relating to the known art and to provide a method and a device for the monitoring, optionally controlling of the microbiological state of a process stream.

A novel method and device for the analysis of process streams have now been developed. The invention is particularly suitable for use in monitoring, and optionally controlling the microbiological state of process streams, especially aqueous process streams.

With microbiological state herein is referred to the activity of all such microorganisms that can influence the dissolved oxygen concentration and/or the rH value in a process stream, and optionally to aerobic or anaerobic conditions in a process stream.

The idea is based on measuring parameters, such as the concentration of dissolved oxygen, and/or the rH, in a process stream. A sample is taken batch-wise from the process to a measuring unit and concentration of dissolved oxygen in the sample and/or rH of the sample is measured during a measuring cycle. The temperature is preferably also measured, as a more precise value for the concentration of dissolved oxygen can then be obtained.

Optionally, soft sensors based on any equation(s) and/or model(s), e.g. on Linguistic Equation (LE) models are preferably used to assist in the interpretation of the measurement data and/or calculated result data. In addition to the data according to the invention, other process data obtained by any known sensors or analyzers may be utilized to give an even more accurate perception of the microbiological state of the process streams for monitoring and optionally controlling the microbiological state of a process stream.

Thus, the present invention concerns a method and a device for monitoring and optionally controlling the microbiological state in a process stream by measuring the concentration of dissolved oxygen or the rH value, or both, in said stream.

More specifically, the method of the present invention is characterized by what is stated in Claim 1.

Further, the device of the present invention is characterized by what is stated in claim 13.

This method and device make it possible to monitor the microbiological state of a process stream, in particular industrial stream, and to optionally control the microbiological state. The microbiological state can be controlled by controlling, preferably automatically, the amount of biocide(s) and/or location of the dosing of biocide(s) and/or selection of the type of biocide(s) to be added to the process stream, with a simple measurement method. The method allows also analysis of process streams with low concentration of dissolved oxygen. It also enables monitoring and optionally controlling the microbiological state of a process stream under anaerobic conditions. The method and the device may provide online data on the microbiological state of the analyzed process stream.

Next, the invention will be described more closely with reference to the attached drawings and a detailed description.

DETAILED DESCRIPTION OF PREFERRED EMBODIMENTS OF THE INVENTION

Figure 1:
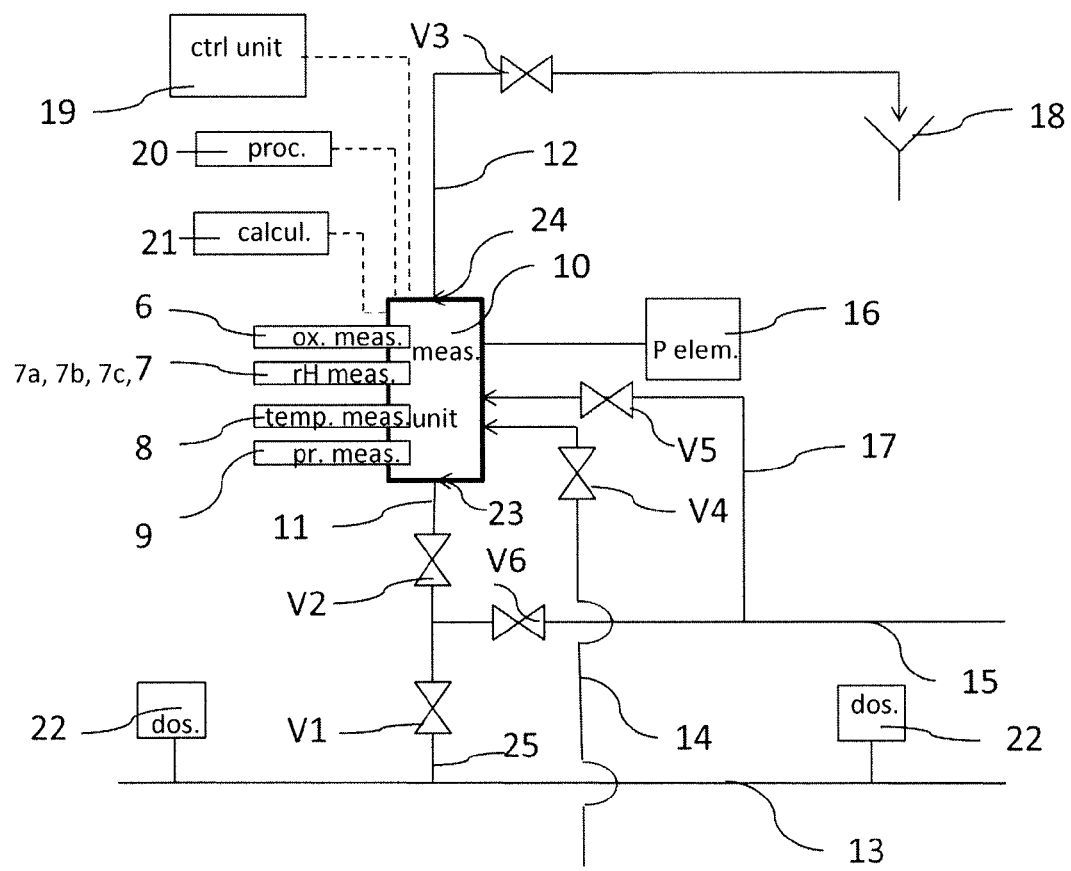
FIG. 1 is a schematic picture of an arrangement to perform an embodiment of the method according to the invention.

The present invention concerns a method and device for monitoring, and optionally controlling the microbiological state, of a process stream preferably of an industrial process by batchwise obtaining a sample of the suspension stream, measuring the concentration of dissolved oxygen or the rH value, or both, in said stream at least at two time points, calculating the relative oxygen consumption, the change of rH or the relative change of the rH, between two of said two or more time points, or calculating two or more of these, and determining microbiological state of the stream based on the measurements, and an device suitable for use in implementing said method.

With the term "microbiological state" of a process stream, is referred to the activity of all such microorganisms that can influence the dissolved oxygen concentration and/or the rH value in a process stream, and optionally to aerobic or anaerobic conditions in a process stream.

Microbiological activity in process streams can be indirectly measured by monitoring the consumption of dissolved oxygen because dissolved oxygen consumption is directly related to aerobic metabolism of the cell. The higher the activity of the microorganisms, the higher the consumption of the dissolved oxygen is. Surprisingly, it was found that the relative dissolved oxygen consumption can be used to monitor microbiological state of a process stream. Relative dissolved oxygen consumption was found to be a very sensitive measurement for microbiological activity in accordance with the method of the invention in the aerobic conditions (i.e. when the concentration of dissolved oxygen is higher than 0 mg/l). Often the relative consumption of dissolved oxygen correlates also with the amount of the aerobic bacteria.

The rH value or especially the change or relative change thereof was found to describe microbiological activity under anaerobic and anoxic conditions. Under anaerobic and anoxic conditions microbes generate such products which tend to decrease rH value of the process stream. The rH value, change or relative change thereof often also correlates with the amount of anaerobic bacteria.

Further, rH value may correlate also in aerobic conditions with the amount of the aerobic bacteria in the suspension stream to be analyzed, especially when strongly oxidative chemicals are substantially absent in the sample. When the oxygen is being consumed by the microbes, the oxygen concentration is decreased and thereby the rH value decreases.

By measuring both concentration of dissolved oxygen and rH value in a process stream according to one embodiment of the invention, information on a wide area of process conditions can be obtained. The value(s) of dissolved oxygen concentration and rH measured at the beginning of a measuring cycle, describe whether the process conditions are anaerobic or aerobic. Thus, changes in a process stream from anaerobic to aerobic conditions, and vice versa, can be obtained.

The initial values at the beginning of the measuring sequence may be used for selecting of the at least one measurement (dissolved oxygen or rH) used for determining the microbiological state. Thus, combining information from the initial values of the measurement cycles or dissolved oxygen concentration and/or rH with one or more of change of rH, relative change of rH or relative change in oxygen consumption, microbiological state of a process stream can be monitored, optionally controlled with the method of the invention both under aerobic and anaerobic conditions. This is especially preferred to be used in a process where the process conditions vary between anaerobic and aerobic process conditions.

An arrangement for performing a preferred embodiment of the method according to the invention is schematically illustrated in FIG. 1.

The device according to the invention contains a measuring unit 10 with an inlet 23 and an outlet 24, means for measuring amount of dissolved oxygen 6 and/or means for measuring rH 7 within the measuring unit, with reference to FIG. 1.

The device preferably contains an inlet conduit 11 for directing a sample to the measuring unit 10. The device may contain an outlet conduit 12 for directing the sample from the measuring unit. The inlet conduit 11 is in connection with a process line 13 whereby the inlet conduit allows taking a side-draw from the main process line 13. The said means 7 for measuring the rH value preferably includes: means 7a for measuring the redox potential, means 7b for measuring the pH value and preferably means 7c for calculating the rH value.

In an embodiment the device includes means 8 for measuring the temperature and optionally means 9 for measuring pressure.

Thus, the device of the present invention is suitable for monitoring, optionally controlling, the microbiological state in a process stream by measuring online the amount of dissolved oxygen or the rH, or both, in said stream.

In a preferred embodiment the device is in fluid connection with a process line 13 for a process stream. Process line 13 is equipped with a side draw 25 which may be the inlet conduit 11 for withdrawing a sample from said process stream, preferably a main process stream. Thereby the side draw 25 functions as a sampling point. The side draw 25 is in fluid connection with a measuring unit 10. The measuring unit is preferably a closed vessel with openings for entrance(s) of the sample flow, exit(s) of the sample, and any opening(s) for process equipment if needed, e.g. measuring probes or sensors, inlets for water or gas lines. Side draw 11 is preferably equipped with valve V1 for sampling from process line 13. The vessel 10 is preferably lacking means for mixing the sample during the measurement. The measuring unit 10 is intended for holding the sample during the measurement. The measuring unit may contain an inlet 14 with valve V4 for pressurized air to provide turbulence to the process stream between any chosen measurement cycle, thereby enabling cleaning of surfaces inside the measuring unit. The cleaning of the surfaces inside the vessel may additionally or alternatively be effected by providing water via inlet line 17 for washing water, including valve V5. In a preferred embodiment the device contains flow inlets only for the entrances of the sample flow to be measured. Further, the device comprises means either for measuring the concentration of dissolved oxygen 6 or for measuring the redox 7a and pH 7b to determine rH of the sample within said measuring unit 10, or both 6, 7, as well as means 20 for processing the measurements and performing calculations based on the measured values (e.g. calculating relative dissolved oxygen consumption, rH, change or relative change of rH).

As stated above, the optional means 7 for measuring the rH of the sample preferably include means 7a for measuring the redox potential of the sample and means 7b for measuring the pH value of the sample, and preferably means 7c for calculating the rH value of the sample, and optionally means for measuring temperature.

The above mentioned means 6 for measuring the concentration of dissolved oxygen are preferably selected from (non-electrochemical) sensors not requiring the use of membranes, as the sensors based on use of membranes become less sensitive with time (through ageing and fouling of the filters) and they require mixing of the sample or sufficient flow rate during the measurement and regular calibration. It is particularly preferred to use sensors utilizing optical measurement technology, e.g. luminescent dissolved oxygen (LDO) technology. The LDO sensors are available e.g. from HACH COMPANY, water analysis technology manufacturer.

As it is preferred to provide temperature and/or pressure control in methods for monitoring the microbiological state of a process stream, the device preferably comprises also means 8 for measuring the temperature of the sample within said measuring unit 10, and preferably also means 9 for measuring the pressure within said measuring unit 10. The means 8 for measuring the temperature are particularly preferred when applying the means 6 for measuring the concentration of dissolved oxygen. These means 6 may include separate means for measuring the temperature, such as a temperature sensor or a thermometer. The means 8 for measuring the temperature are particularly also preferred when applying the means 7 for measuring the rH.

The measuring unit may thus include means for measuring temperature of the sample within the vessel. Optionally, means 6 for measuring the concentration of dissolved oxygen and/or means for measuring rH of the sample may include additional means for measuring temperature.

It is also preferred to include into the device means 19 for controlling and monitoring the function of the device. This control and/or monitoring can take place on site or using a remote system. These means 19 are used, among others, for controlling the cycles and sequences of cycles, for temperature control, for controlling the calculations (e.g. controlling the processing of the measurement) and for controlling the dosing of biocide(s). According to a preferred embodiment of the invention, the device further comprises means 21 for calculating the amount of biocide to be added into the process line 13, and means 22 for dosing said biocide into the process line 1.

According to a particularly preferred embodiment of the present invention, the device includes a temperature controlled measurement vessel 10, inlet conduit 11 and washing line 15 with supplementary equipment, e.g. to regulate the flows in said lines (e.g valves V1, V2, V6), as well as a control unit 19. Since dissolution of oxygen in liquid e.g. water depends on the temperature, the temperature of the measurement reactor 10 is monitored and optionally controlled. The heating and/or the cooling of the measuring unit 16, that are required if the measurements are run at constant temperature, are realized using, e.g. Peltier elements. The measurement vessel 10 is heated, e.g. by the electric resistance of the Peltier elements, and cooled by the cooling water circulation of the elements. If the temperature during the measurement is not constant or controlled, the effect thereof on the dissolution of oxygen can be compensated by calculations. Also an oxygen measurement sensor 6 and a temperature sensor 8, such as a PT-100 sensor, are installed in the vessel 10. The temperature sensor 8 is used to monitor the temperature of the vessel 10.

In a preferred embodiment a sampling system comprises at least an inlet conduit 11, at least means (e.g. valve(s)) to regulate the sample flow between a process stream 13 and a measuring unit 10, and preferably an outlet conduit 12.

In a preferred embodiment a sampling line washing comprises at least a washing line 15 and at least means to regulate the washing water flow (e.g. valve V6 and V1) between a process stream 13 and a washing line 15.

Since pressure influences dissolution of oxygen in liquid e.g. water, in a preferred embodiment the pressure of the measuring unit 10 is monitored and optionally controlled. Measurements of the dissolved oxygen and/or rH are preferably carried out in the normal air pressure. Normal air pressure can be obtained into the measurement vessel by opening valve V3 of the outlet conduit (12) before the measurement starts or by having the outlet conduit open to the normal pressure. In a preferred embodiment the V3 is not in the system.

In a preferred embodiment the means 20 for processing the measurements and performing calculations based on the measured values, means 19 for controlling and monitoring the function of the device and means for 21 for calculating the amount of biocide(s) are included in a same system, e.g. programmable logic and/or industrial PC.

A preferred device includes a measuring unit, online-sensors, sampling line washing, sampling systems, and programmable logic and/or industrial PC for processing the measurement results, controlling and monitoring the function of the device and for calculation the amount of biocides to be added into the process line.

The measured and/or calculated values according to the invention may be monitored locally or via a remote system, e.g. web-based.

The method of the present invention for monitoring the microbiological state, in a process stream, includes the steps of
  providing a process stream originating from an industrial process;
  batch-wise conducting a sample of the process stream, preferably from a sampling point, to a measuring unit;
  measuring the concentration of dissolved oxygen or the rH, or both, in the sample within the measuring unit as a function of time, preferably at least at two time points;
  calculating relative oxygen consumption, or change of rH or relative change of the rH between two of said two or more time points, or calculating two or more of these; and
  determining, based on the rH value or on one or more of these calculated values, the microbiological state of the process stream.

Another embodiment of a method of the present invention of monitoring the microbiological state, in a process stream by measuring the concentration of dissolved oxygen or the rH, or both, in said stream, the method comprising
  providing a process stream originating from said process;
  batch-wise conducting a sample of the process stream, preferably from a sampling point, to a measuring unit;
  measuring, at two or more time points, the concentration of dissolved oxygen or the rH, or both, in the sample in the measuring unit;
  determining, based on one or more of calculated values or rH value, the microbiological state of the process stream, wherein the calculated values include calculating relative oxygen consumption, or change of rH or relative change of the rH, or rate of the change of rH or consumption of dissolved oxygen between two of said two or more time points, or calculating two or more of these.

Optionally, the determined microbiological state in said stream is used to optimize the biocide program, e.g. to select a biocide or biocides and/or calculate an amount or dose of biocide(s) to be added into the process stream and/or to select the location of the addition point(s) of the biocide(s). It can also be used to identify the location and/or source of microbiological problems in a system of which the process stream is a part of, such as pulp, broke, water circulation and raw water, which can be present in, e.g. tanks, containers, pulpers and pipes.

Optionally, the determined microbiological state in said stream is used to control, preferably automatically, the microbiological state of the process stream by controlling the amount of biocide(s) added to the process stream, the selection of points of addition, or selection of the type of biocide(s) or any combination of the three. Preferably the controlling of microbiological state in said stream includes controlling the amount of biocide(s) added to the process stream, preferably by an automated control system.

In a preferred embodiment of the invention the method further comprises controlling of microbiological state in said process stream by adding an amount of biocide(s) to the process stream, preferably by an automated control system.

By using the invention, it was found in a paper or board manufacturing process, that a stage that is ideal for microbial growth was the broke tank, where the broke can be stored for long periods of time, such as 2-10 h, or even days.

The determined microbiological state may also be used to determine and control the desired delay time of process streams, such as the broke of a paper or board manufacturing process, in various tanks, since a shorter delay time might be required, for example, if there is a large increase in the microbe growth within said tank.

According to a preferred embodiment of the invention, the device according to the invention is used in the implementation of this method.

The process stream to be analyzed may be any aqueous or non-aqueous liquid, optionally comprising solid matter. The solid matter can be in suspended and/or colloidal form. The process stream is particularly a process stream in a water circulation system of an industrial process, any aqueous suspension, such as paper or board pulp, wastewater, paper coating colour, activated sludge, inorganic sludge, or washing streams, such as the ones used in oil drilling or mining. The process stream may originate from an industrial water system or municipal water system. According to a preferred embodiment of the invention, the stream consists of paper or board pulp suspension including optional additives.

A process stream may be a flow or a stream in a process or stagnant, e.g. sample or content of a storage tank.

Figure 2:
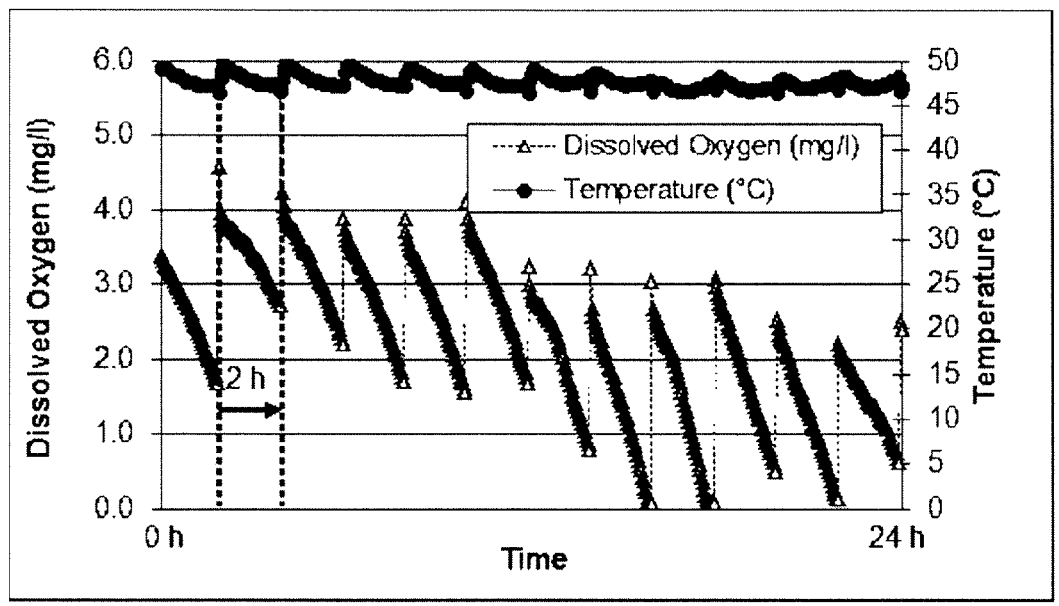
FIG. 2 is a graphical illustration of exemplary outputs of the online-measurement device of the present invention, showing the concentration of measured dissolved oxygen in the measurement unit and the temperature.

According to a preferred embodiment of the present invention, batch-wise sampling is used. A process stream is conducted to a measuring unit. When the measuring unit is filled with the process stream sample, the flow is interrupted to keep the sample in the measuring unit. The sampling is usually performed conducting a process stream through the measuring vessel for a period of time (sampling time) to obtain a representative sample. After sampling the flow is interrupted to keep the sample in the measuring unit. The sample is kept in the measuring unit for a period of time, i.e. a measuring cycle. Measurements are performed at least at two time points during a measuring cycle. The time used for the measuring cycle is evaluated based on the general (average) microbiological state of the stream to be analyzed. Preferably the measuring cycle varies between 1 minutes and 3 hours, more preferably between 15 minutes and 2 hours. An example of the output of measurements is shown in FIG. 2. In this exemplary system the sampling time was 15 s and measuring cycle of dissolved oxygen was 2 h. In a preferred embodiment the measurements are performed during the whole measuring cycle, e.g. a measurement value is recorded 60 times per minute during the measuring cycle, e.g. during two hours.

The values measured (concentration of dissolved oxygen or a combination of pH and redox potential, or both of these) at least at the two time points are used to calculate the oxygen consumption ($\Delta DO$), the relative oxygen consumption ($\Delta DO$ %), rH value (rH), the change of the rH value ($\Delta rH$) and/or the relative change of the rH value ($\Delta rH$ %).

The oxygen consumption (mg/l) is calculated using equation (1):

$$\Delta DO = O_2(t_1) - O_2(t_2) \qquad (1)$$

and the relative oxygen consumption (%) is calculated using equation (2):

$$\Delta DO\ \% = 100\% \cdot \frac{O_2(t_1) - O_2(t_2)}{O_2(t_1)} \quad (2)$$

where $O_2(t_1)$ is the first value of the concentration of dissolved oxygen. The first value is preferably measured at the beginning of the measuring cycle, e.g. within the first 15 minutes thereof. $O_2(t_2)$ is the second value of the concentration of dissolved oxygen. The second value is preferably measured at the end of the measuring cycle, e.g. within the last 15 minutes of the measuring cycle.

The redox value is pH dependent. The rH value is calculated from the pH and redox potential using equation (3):

$$rH = 2*pH + 2*Eh*F/(c \cdot R \cdot T) \quad (3)$$

wherein F=Faraday constant $(9.64853399(24) \times 10^4$ C mol$^{-1}$, c=ln 10, T=temperature (K), Eh=redox potential measured with standard hydrogen electrode, and R=universal gas constant $(8.314472(15)$ J K$^{-1}$ mol$^{-1}$).

Figure 7:
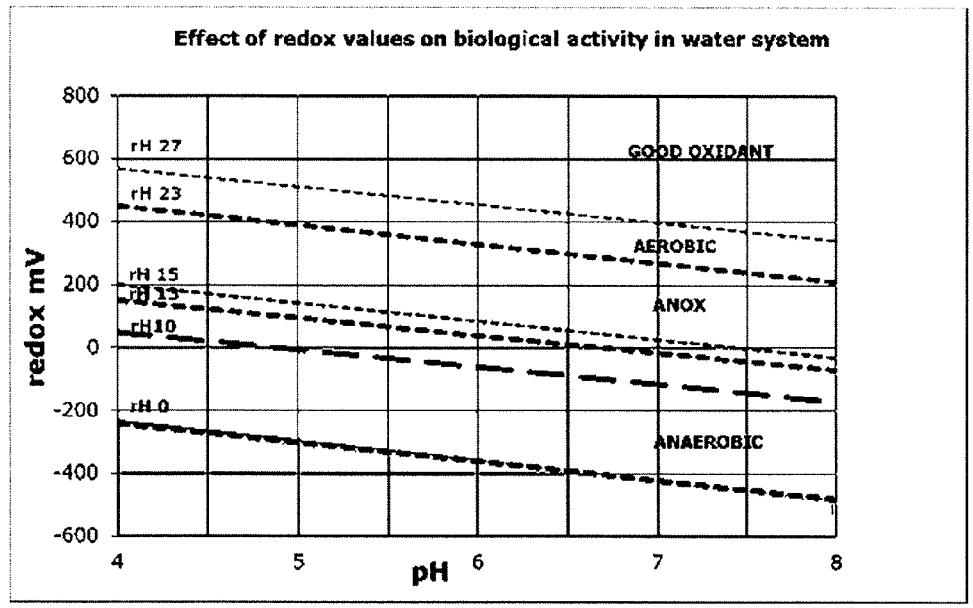
FIG. 7 is a graphical illustration of the effect of the pH on the redox value, as well as rH values corresponding to different process conditions, e.g. aerobic or anaerobic conditions.

In the exemplary system of FIG. 7, when T=20° C. (293 K).

$$rH = Eh/0.029 + 2*pH \quad (4)$$

In this exemplary system, assuming that pH=6.5 and Eh=−0.15V:

$$rH \sim 7.8$$

Further, as above for the oxygen consumption, the change of the rH value can be calculated using the following equation (5):

$$\Delta rH = rH(t_1) - rH(t_2) \quad (5)$$

and the relative change of the rH value (%), using the following equation (6):

$$\Delta rH\ \% = 100\% \cdot \frac{rH(t_1) - rH(t_2)}{rH(t_1)} \quad (6)$$

where $rH(t_1)$ is the first rH value. First rH value is preferably measured at the beginning of the measuring cycle, e.g. within the first 15 minutes thereof $rH(t_2)$ is the second rH value and measured after the first value. The second rH value is preferably measured at the end of the measuring cycle, e.g. within the last 15 minutes thereof.

By recording more than two values the method and device of the present invention allow also online monitoring of the measured rH value and/or concentration of dissolved oxygen (as shown in FIG. 2) during a measurement cycle. By using at least two, preferably more than two values of the measurements, thus allow a determination of, among others, the rate of oxygen consumption and/or rate of rH change during a measurement cycle. The rate of oxygen consumption and/or rate of rH change may also be used for selecting time period suitable for the measurement cycle and/or monitoring the microbiological state of the process stream.

The method is preferably carried out using a sequence of cycles, the cycles including at least one sampling cycle and at least one measuring cycle, preferably consisting of one sampling cycle and one measuring cycle. Thereby the method according to one embodiment of the invention can be considered a continuous method. In one embodiment the next cycle follows the previous substantially immediately. The sampling cycle is usually shorter than the measuring cycle. Sampling time depends on the process, and may be e.g. between 60 seconds and 2 minutes. A suitable sampling time can be determined by a person skilled in the art. There can also be a time period between the cycles (after one sampling and measuring cycle has ended), e.g. if it is enough to receive monitoring data of the process stream only some times per day.

Figure 8A:
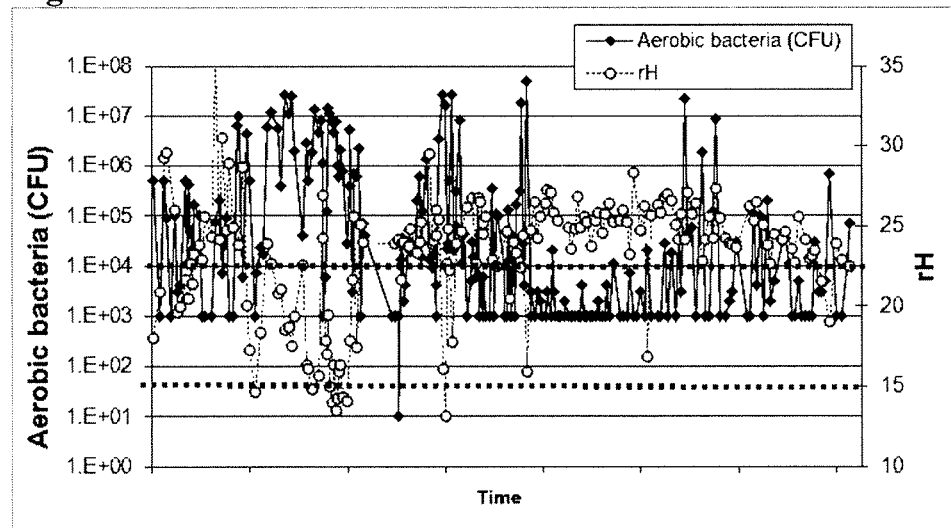
FIG. 8*a* and FIG. 8*b* are is a graphical illustration of the amount of microbes at different rH values, FIG. 8*a* showing a measured rH values over a period of time, where the number of aerobic bacteria increases as the rH value decreases, and FIG. 8*b* showing the measured rH value versus amount (CFU) of anaerobic bacteria measured in the laboratory.
Figure 8B:
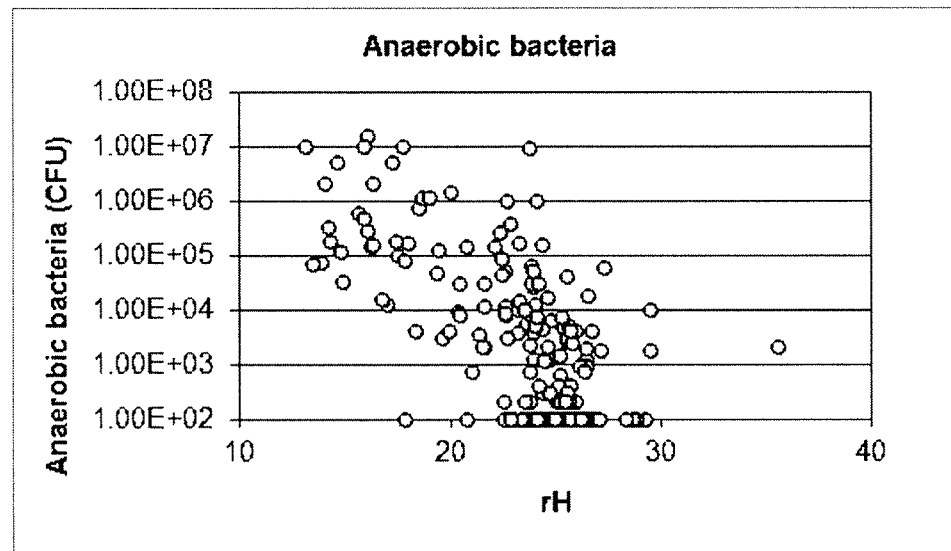

In a particular embodiment of the invention a process stream is conducted to a measuring unit without interrupting the process flow, and the rH value of the process flow is measured during the flow. The rH value is used to monitor, optionally control, the microbiological state of the process flow. It is preferred to utilize this embodiment especially for inorganic sludges, such as coating colors. FIG. 8b show that rH value as such correlates with amount of anaerobic bacteria. rH may also correlate with amount of aerobic bacteria in some process streams, as shown in FIG. 8a. However, in case of changes in the process flow other than microbiological, the rH value as such may not provide information on the microbiological state alone.

To provide further control of the method, and an even more reliable result, the temperature of the sample and optionally the pressure in the measuring unit is measured. This is particularly useful when determining the microbiological state of the sample using the concentration of dissolved oxygen, as the dissolution of oxygen into liquid, e.g. water is temperature dependent and also pressure dependent. To take this dependency into account, the method can either be carried out at constant temperature, or the measured temperature can be included in the subsequent calculations to compensate for any changes in the temperature. The same applies for the pressure in the measuring unit during the measurement. However, it is preferred to carry out both the measurement of the concentration of dissolved oxygen and the measurement of the rH at least at constant pressure, preferably at ambient pressure, which usually is normal air pressure, but most preferably also at constant temperature. In a still preferred embodiment of the invention the pressure and temperature in the measurement vessel during the measurement are kept constant.

Thus, by determining the relative consumption of dissolved oxygen in a process stream, such as paper or board pulp, for example the pulped broke of a paper machine, conclusions can be made regarding the microbiological activity in the process stream, e.g. the pulp, and also amount of oxygen consuming microbes, particularly aerobic bacteria, in the process stream, e.g. the pulp. Similarly, by determining the rH, change of rH or relative change of rH in a process stream, such as, paper or board pulp suspension, conclusions can be made regarding the microbiological activity in the sample, and also amount of aerobic/anaerobic microbes in the sample.

Based on the conditions at the beginning of a measuring cycle it can be decided (preferably automatically) which at least one of the two measurements (the concentration of dissolved oxygen or the rH value) is used for determining the microbiological state of the process stream. In aerobic conditions (concentration of dissolved oxygen is higher than about 0 mg/l) it is preferred to measure concentration of the dissolved oxygen in the sample and use relative consumption of dissolved oxygen to determine the microbiological state of process stream. In anaerobic or anoxic conditions (concentration of dissolved oxygen is about 0 mg/l) it is preferred to measure rH value of the sample and use change or relative change of rH to determine the microbiological state of process stream.

According to a preferred embodiment of the present invention, both concentration of the dissolved oxygen and the rH value are measured.

The initial value(s), preferably value(s) measured at the beginning of the measuring cycle, of dissolved oxygen concentration and rH describe whether the process conditions are anaerobic or aerobic and may be used for selecting of the at least one measurement (dissolved oxygen or rH) used for determining the microbiological state.

According to an embodiment of the invention, measurement of initial value(s) of the concentration of dissolved oxygen or the rH is carried out at the beginning of or before (e.g. during the sampling) the measurement cycle to determine whether the process stream conditions are aerobic or anaerobic. The results obtained in this initial measurement(s) are preferably interpreted and used in selecting, preferably automatically, a suitable measurement parameter from the concentration of dissolved oxygen, the rH or their combination for a measurement cycle, preferably current or next, or any following measuring cycle, and optionally used to control the microbiological state of the process stream. Carrying out initial measurement of the concentration of dissolved oxygen or the rH at the beginning of the measurement cycle may be effected by analyzing one or several initial measurement values at the beginning of a measurement cycle, e.g. within the first 60 seconds of the measurement cycle. Thereby the suitable measurement parameter from the concentration of dissolved oxygen, the rH or their combination can be selected for the ongoing measurement cycle. The initial value can also be the value, first value, which is used in the calculations of change of rH, relative change of rH and/or relation oxygen consumption change.

In the present invention it is preferred that the measurement takes place online, as this makes it possible to react to the effects of temporary changes in the microbiological state of the analyzed stream.

The concentration of dissolved oxygen in the process stream and/or the rH in the process stream can also be measured before taking the sample to or before it searches a measuring unit or during the process stream flows through the measuring unit. One or more of the said measurements obtained outside the measurement cycle can be used for monitoring, optionally controlling the microbiological state of the process stream as such or in combination with the calculated values obtained from the measurements outside the measuring cycle.

Figure 3:
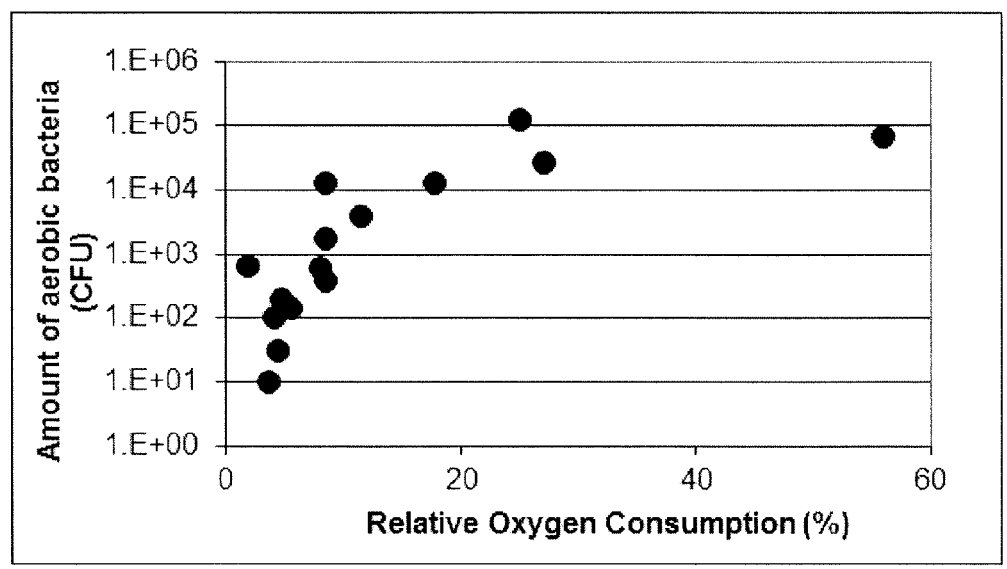
FIG. 3 is a graphical illustration of the relative oxygen consumption and the amount of aerobic bacteria in an exemplary pulp suspension.

Often the relative dissolved oxygen consumption in a process stream correlates with the amount of aerobic bacteria in the process stream. FIG. 3 shows relative oxygen consumption values determined with a method according to the invention vs. amount of aerobic bacteria on the sample, measured using the plate count method. When amount of microbes is high, the relative oxygen consumption during the measuring cycle is high. When the amount of microbes is low the relative oxygen consumption is small.

Oxygen can be consumed also by chemical oxidation reactions or oxygen can be released in chemical reactions (e.g. decomposition of $H_2O_2$). Chemical reactions have strongest effect immediately after chemical addition and usually require presence of strong oxidants. The effect of chemical reactions on the estimation of the microbiological state of a process stream can be taken into account or eliminated by selecting the measurement or sampling location. A person skilled in the art is capable of taking this into account.

Also the rH value of a process stream can be affected by changes in a process stream other than microbiological changes, such as changes in the bleaching of process flow or addition of strong oxidative chemicals. By measuring the change or relative change of the rH according to the invention the effect of the changes other than due to microbiological changes in the quality of a process stream can be eliminated. The effect of chemical reactions on the estimation of the microbiological state of a process stream can be taken into account or eliminated by selecting the measurement or sampling location. A person skilled in the art is capable of taking this into account.

Figure 4:
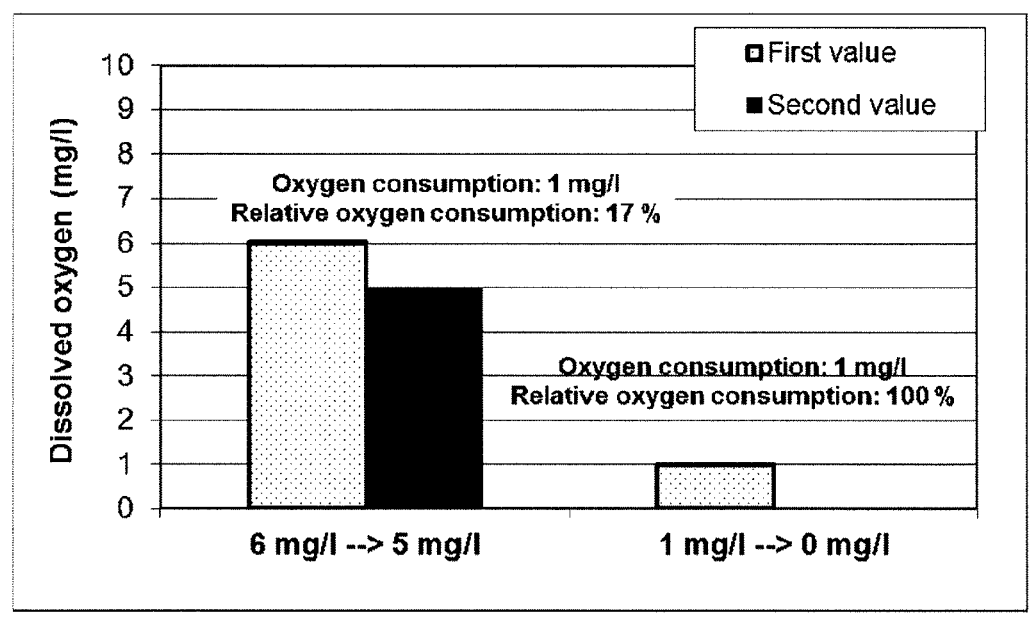
FIG. 4 is a graphical illustration of the oxygen consumption (mg/l) and the relative oxygen consumption (%) of an exemplary pulp sample between $t_1$ and $t_2$ in the measuring cycle.

FIG. 4 shows examples of two measuring cycles where concentration of the dissolved oxygen (mg/l) in the sample was recorded. In the first example the first value at the beginning of measuring cycle is 6 mg/l and the second value at the end of measuring cycle is 5 mg/l. Oxygen consumption during the measuring cycle is thus 1 mg/l and relative oxygen consumption 17%. In the second example the first value at the beginning of measuring cycle is 1 mg/l and the second value in the end of measuring cycle is 0 mg/l. Oxygen consumption during the measuring cycle is 1 mg/l and relatively oxygen consumption 100%. In the first example the overall level of the concentration of the dissolved oxygen is high and the oxygen consumption as well as the relative oxygen consumption is quite low. This indicates that the microbiological activity is low and amount of bacteria is low whereby the microbiological state is good. In the second example the high relative oxygen consumption indicates poor microbiological state probably resulting from high activity of aerobic bacteria. In both examples the oxygen consumption is the same 1 mg/l. However, relative oxygen consumption in the two examples differs significantly.

Figure 5A:
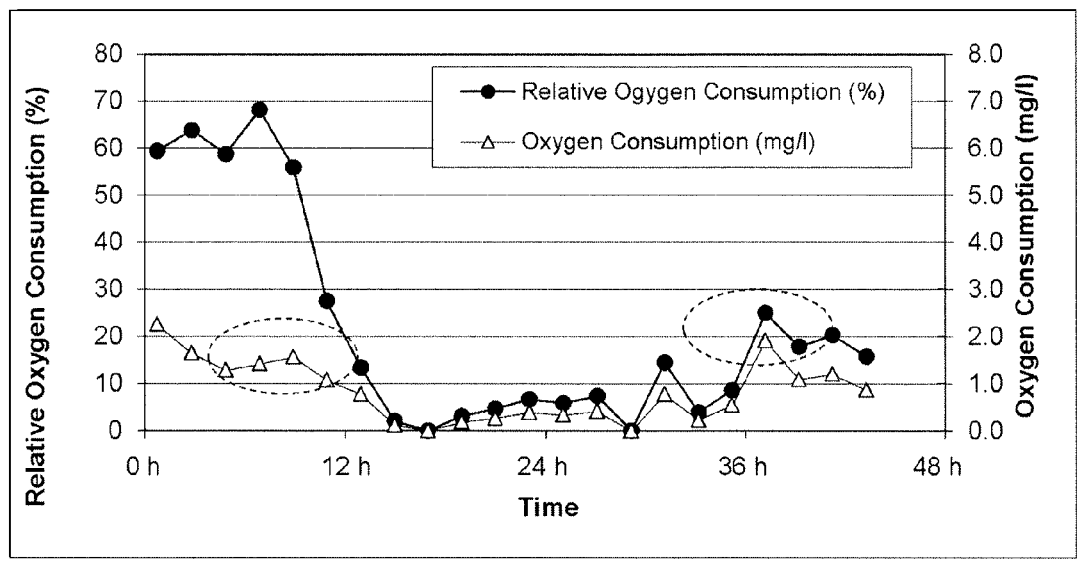
FIG. 5*a* is a graphical illustration of the relative oxygen consumption and the oxygen consumption in an exemplary pulp sample at different moments of time during a measurement.
Figure 5B:
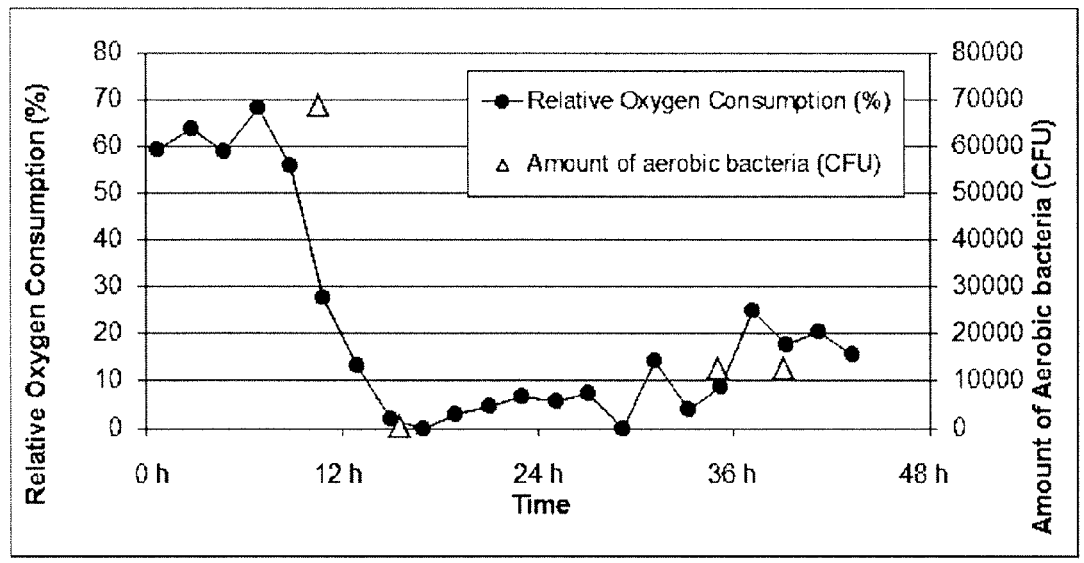
FIG. 5*b* shows the relative oxygen consumption and the amount of aerobic bacteria in the same exemplary pulp suspension.

FIG. 5a is a graphical illustration of the relative oxygen consumption and the oxygen consumption in a pulp process stream as a function of time. FIG. 5b shows the relative oxygen consumption and the amount of aerobic bacteria in the same exemplary process stream. The values of the oxygen consumption and relative oxygen consumption are obtained from sequential measurement cycles.

In the results, FIG. 5a shows a significant change in the relative oxygen consumption (%) as a function of time while the oxygen consumption (mg/l) remains nearly unchanged. FIG. 5b shows that a significant change occurs also in the amount of aerobic bacteria. Thus, relative oxygen consumption may be used to give reliable information of the microbiological state of the process stream.

Thus, if monitoring only the oxygen consumption (mg/l), there is a risk that an alarming situation regarding the microbial state of a process stream is not noticed. Thereby, the amount of required biocides can be reliably controlled based on the relative oxygen consumption (%).

In addition the other parameters obtained by commercially available sensors or analyzers, such as temperature sensors, pH sensors, ion selective electrodes, for example for the analysis of chlorine and bromine, and anode stripping voltammetry for measuring the concentrations of heavy metals, and any known surface fouling sensors or analyzers may be utilized to give additional information of the microbiological quality of the process streams.

Figure 6:
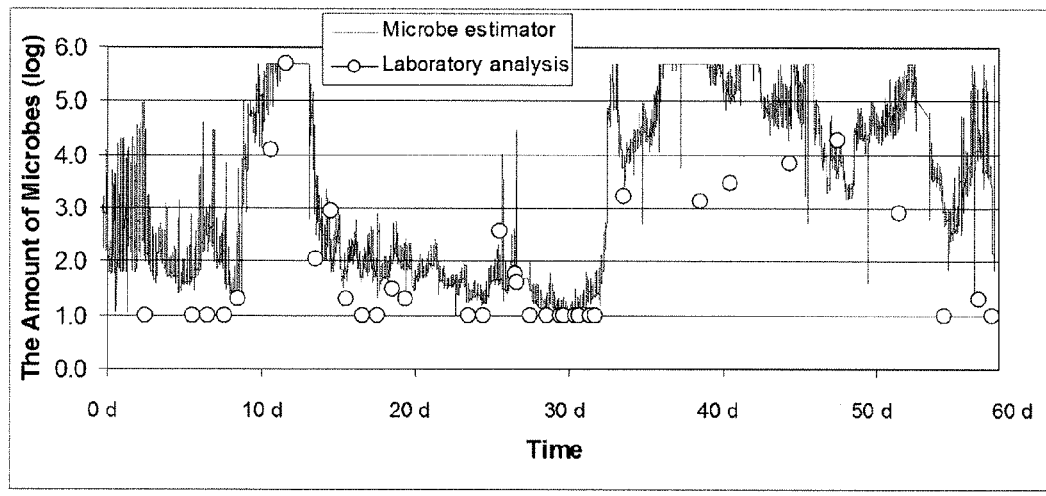
FIG. 6 is a graphical illustration of the amount of microbes in an exemplary pulp suspension, as measured using a conventional laboratory analysis method and estimated using a soft sensor based on linguistic equations.

Soft sensors are preferably implemented in the method according to the invention. Soft sensors are additional estimation systems utilizing calculations to provide more detailed results of the microbiological state of a process. Soft sensors, e.g. based on Linguistic Equation (LE) models are preferably used to assist in the interpretation of measurement or calculated data, particularly in the method step of determining the microbiological state of the suspension, by providing equations used in calculations. The said data may be data obtained according to the method of the invention or other process measurements obtained by any known sensors or analyzers. For example the amount of microbes after chemical treatment can be predicted on the basis of the rH value and the amount of biocide residual using a soft sensor. The results of a soft sensor may be used as such or in combination with the method according to the invention to monitor, and optionally control the microbiological state of a process stream. An exemplary result of a model based on soft sensors is shown in FIG. 6, as compared to the results of a laboratory analysis.

In a preferred embodiment of the invention the method further comprises controlling the microbiological state in said process stream by adding an effective amount of biocide(s) to the process stream, preferably by an automated control system.

In some preferred embodiments of the invention feedforward (FF), feedback (FB) control and/or FB controller with a cascade loop are used for controlling the microbiological state of the said process stream.

The measurements for the determination of the microbiological state according to the invention can be carried out on a sample of the process stream taken either before the stream reaches a point of biocide dosing in the process stream, or after this point. The output(s) of the method according to the invention can be used in dosing control of biocides (amount, type of, location). According to a preferred embodiment, the sample is taken before the stream reaches the biocide dosage point, and the results are used to control the subsequently required amount of biocide dose to be added to the process stream (i.e. feedforward (FF) control in FIG. 9). According to a preferred embodiment, the sample is taken after the biocide has been added, and the results are used to determine the success of the biocide treatment. Also in the latter case, the results may be used to control the required amount of biocide dose (i.e. feedback (FB) control, FIG. 10).

Figure 9:
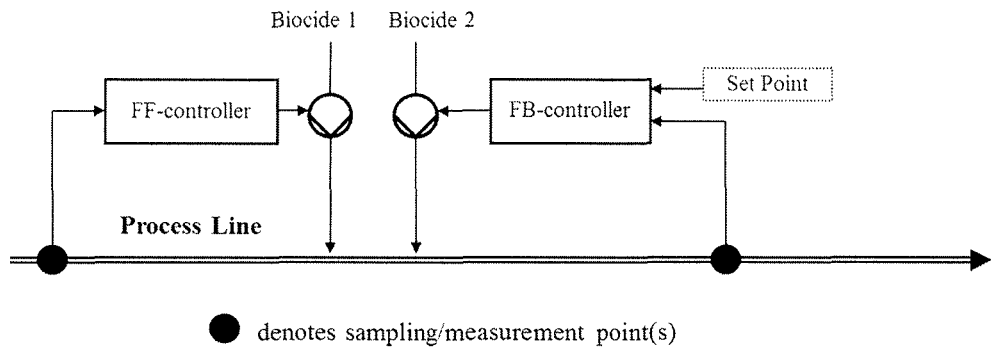
FIG. 9 is a schematic picture of an exemplary control strategy based on measurement(s) according to the present invention in a suspension stream intended to undergo a two-step biocide treatment, with two separate addition points.
Figure 10:
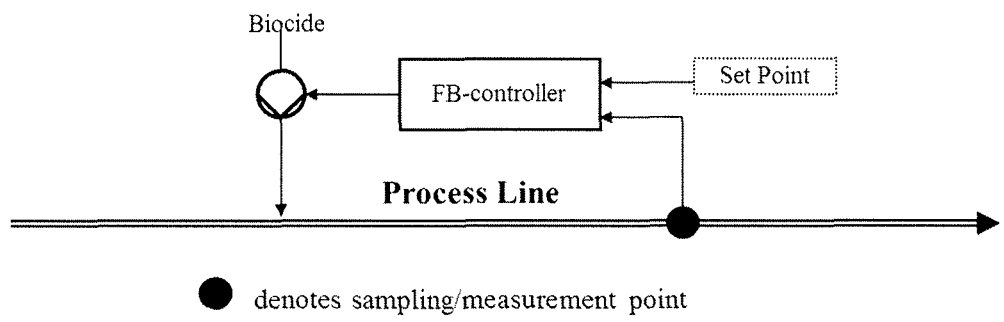
FIG. 10 is a schematic picture of an exemplary control strategy (for a basic feedback FB controller) based on measurement(s) according to the present invention in a suspension stream intended to undergo a one-step biocide treatment.

According to an alternative embodiment of the invention, samples are taken from the stream both before and after two points of biocide dosage as shown in FIG. 9. Thus, there is provided a feedforward as well as a feedback control of the required amount of biocide addition. The said points of biocide dosages may dose the same or different types of biocides. Samples may be taken from the stream both before and after one or several point(s) of biocide addition.

Figure 11:
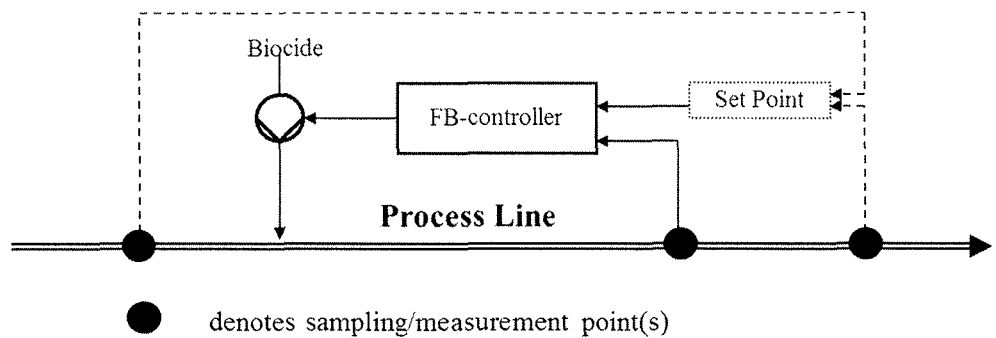
FIG. 11 is a schematic picture of an exemplary control strategy (for an FB controller with a cascade loop) based on measurement(s) according to the present invention in a suspension stream intended to undergo a one-step biocide treatment.

According to an alternative embodiment of the invention, samples are taken from the stream both before and after a point of biocide dosage. FIG. 11 is a schematic picture of an exemplary control strategy (for an FB controller with a cascade loop) based on measurement(s) according to the present invention in a suspension stream intended to undergo a one-step biocide treatment. For controlling the set point value of the feedback controller a measured data and/or calculated data and/or other process measurements from before or/and after the point of biocide addition may be used.

Optionally other process measurements obtained by any known sensors or analyzers, such as temperature sensors, pH sensors, ion selective electrodes, and anode stripping voltammetry for measuring the concentrations of heavy metals, dissolved oxygen sensor and any known surface fouling sensors or analyzers may be utilized in dosing control of biocides. Optionally one or more of the above stated measurements in addition to one or more results of calculations according to the invention (e.g. change in rH or relative change in rH, and relative dissolved oxygen consumption) may be used in the soft sensor calculations, and subsequently in the biocide dosage calculations.

A Linguistic Equation (LE) based soft sensors and online-measurements or calculations, such as measurements of the temperature, the dissolved oxygen, or the rH, and calculations of the relative oxygen consumption, and the change or relative change in the rH value, are preferably utilized in the soft sensor calculation, and subsequently in the biocide dosage calculations.

As regards to an example of suitable equipment we refer to the method and apparatus for automatic dose control of chemicals, described in WO 2005/022278, the contents of which are herewith incorporated by reference.

The operation of a device according to the invention is further illustrated in the following example:

EXAMPLE

Figure 12:
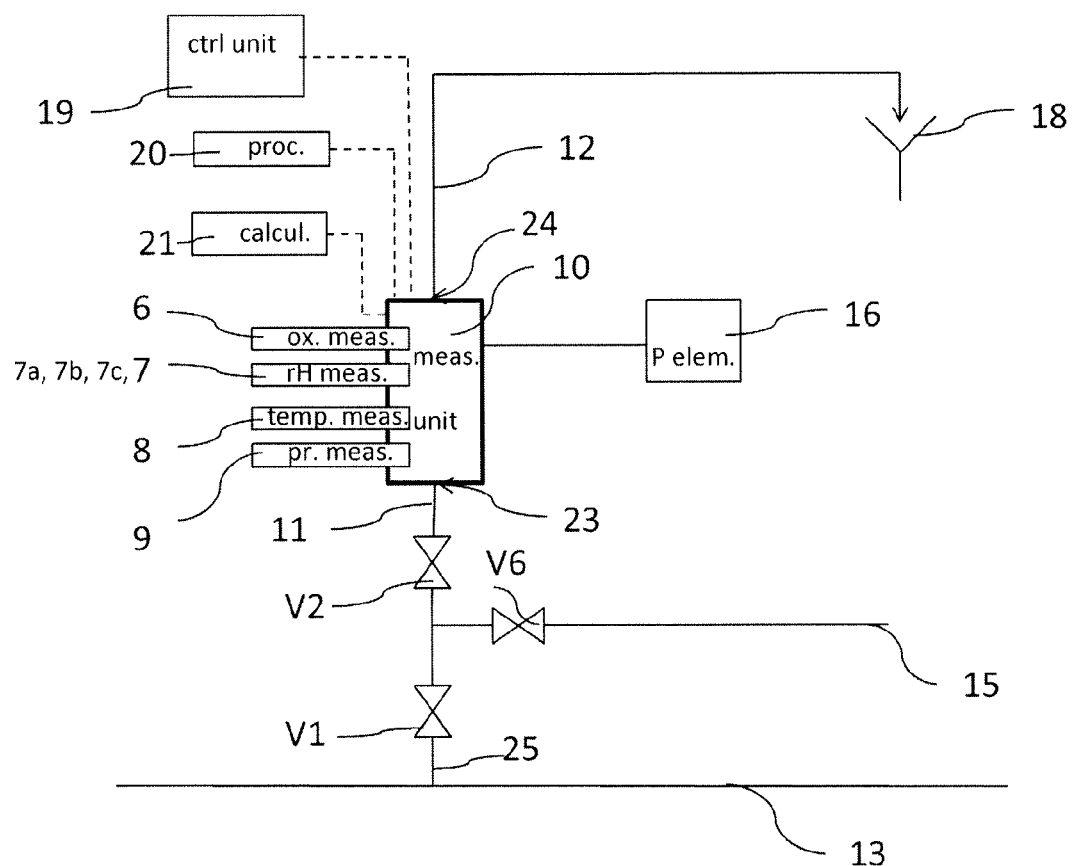
FIG. 12 is a schematic picture of an arrangement to perform an embodiment of the method according to the invention.

In an exemplary process according to an embodiment of the invention is carried out using the configuration of FIG. 12. The device is controlled in accordance with the following programmed sequence, including sequential cycles of sampling, measuring and line washing.

For the purpose of sampling, the valves V1 and V2 are opened, whereby the sample flows through the measuring unit. The sampling cycle lasts for about 15 seconds, after which the valves V1 and V2 are closed.

The measurement cycle begins upon closing of valves V1 and V2, and lasts for about 2 h.

The temperature of the sample in the measurement vessel is maintained at a constant level using a Peltier element 16 for temperature control. As a set point of the controller is used a a value, which is provided by a PT-100 sensor 8 when 1 minute has passed after the start of the measuring cycle.

In this Example, the first value of the concentration of the dissolved oxygen is read after 5 minutes from the start of the measurement cycle, and the second value is read at the end of the measuring cycle. The difference between the first value and the second value are used for the calculation of the relative oxygen consumption.

Simultaneously with the measurement cycle, a sampling line wash is started by opening valves V1 and V6. Washing water is conducted to the sampling line 11 and finally to the main process line 13. Valve V2 is kept closed. The cycle lasts for 12 seconds. Once the line washing ends, the valves V1 and V6 are closed.

Outlet conduit 12 is open to the drain 18 whereby ambient, normal air pressure is present in the measurement vessel. Thus no pressure control is needed.

When the measurement cycle is completed, a new sampling cycle is started by opening valves V1 and V2 whereby the measuring unit is discharged.

The results obtained using a similar programmed sequence, with the same time period used for the measurement cycle, is shown in FIG. 2.

The invention claimed is:

1. A method of monitoring a microbiological state of a process stream by measuring concentration of dissolved oxygen and determining a rH value in said stream, wherein the rH value is determined by measuring a pH and a redox potential of a sample of the process stream and by calculating the rH value by adding the measured pH and redox potential of the sample together, modified by constants, the method comprising
  providing a process stream originating from said process;
  conducting a sample of the process stream to a measuring unit;
  carrying out initial measurements of the concentration of dissolved oxygen and the rH value in the measuring unit at the beginning of the measurement of the concentration of dissolved oxygen and the determination of the rH value, and determining whether process stream has aerobic or anaerobic conditions;
  measuring, in the measuring unit, at two or more time points, the concentration of dissolved oxygen in the sample and calculating relative dissolved oxygen consumption if the process stream has aerobic conditions between the two of said two or more time points;
  determining, in the measuring unit, at least at two time points, which may be the same or different than the at least two time points for measuring the concentration of dissolved oxygen, the rH value of the sample and calculating at least one of change of the rH value and relative change of the rH value if the process stream has anaerobic conditions between said at least two time points;
  determining the microbiological state of the process stream, based on one or more of the rH value, the change of the rH value and the relative change of the rH value if the process stream has anaerobic conditions, and determining the microbiological state of the process stream, based on relative dissolved oxygen consumption and optionally based on the rH value if the process stream has aerobic conditions;
  correlating the relative dissolved oxygen consumption and optionally the rH value to the amount of aerobic bacteria in the process stream, and correlating one or more of the rH value, the change of the rH value and the relative change of the rH value to the amount of anaerobic bacteria in the process stream;
  the method further comprising controlling the microbiological state of the process stream by adding an amount of biocide(s) to the process stream based on results of the correlating the relative dissolved oxygen consumption and optionally the rH value to the amount of aerobic bacteria in the process stream, and correlating one or more of the rH value, the change of the rH value and the relative change of the rH value to the amount of anaerobic bacteria in the process stream.

2. The method according to claim 1, wherein the process stream is an industrial stream.

3. The method according to claim 1, wherein a temperature of the sample of the process stream and a pressure in the measuring unit are measured.

4. The method according to claim 1, wherein the measurement of the concentration of dissolved oxygen or the determining of the rH value, or both, is carried out at constant pressure, or at constant temperature, or with both the temperature and the pressure being constant.

5. The method according to claim 1, wherein the process stream has aerobic conditions if the concentration of dissolved oxygen is higher than about 0 mg/l, the process stream had anaerobic conditions if the concentration of dissolved oxygen is about 0 mg/l.

6. The method according to claim 1, wherein the step of determining the microbiological state of the process stream includes calculations using the following equation for the relative dissolved oxygen consumption:

$$\Delta DO \ \% = 100\% \cdot \frac{O_2(t_1) - O_2(t_2)}{O_2(t_2)} \quad (2)$$

where $O_2(t_1)$ is a first value of the concentration of dissolved oxygen, and $O_2(t_2)$ is a second value of the concentration of dissolved oxygen,
and optionally the following equations for the rH values:

$$rH = 2*pH + 2*Eh*F/(c \cdot R \cdot T) \quad (3),$$

wherein F=Faraday constant $9.64853399(24) \times 10^4$ Cmol$^{-1}$, c=ln 10, T=temperature (K), Eh=redox potential measured with standard hydrogen electrode, and R=universal gas constant $8.314472(15)$ JK$^{-1}$mol$^{-1}$, $$\Delta rH = rH(t_1) - rH(t_2) \quad (5)$$
and
$$\Delta rH \ \% = 100\% \cdot \frac{rH(t_1) - rH(t_2)}{rH(t_1)}. \quad (6)$$

wherein $rH(t_1)$ is a first rH value, and $rH(t_2)$ is a second rH value measured after the first rH value.

7. The method according to claim 1, wherein soft sensors based on Linguistic Equation (LE) models, are used to assist in the interpretation of
  measurement data obtained from the measuring at the two or more time points the concentration of dissolved oxygen,
  determined data obtained from the determining at the two or more time points the rH value of the sample, and
  calculated data obtained from the calculating the relative dissolved oxygen consumption or the change or the relative change of the rH value between the two of said two or more time points,
  to determine the microbiological state of the process stream.

8. The method according to claim 1, further comprising controlling the microbiological state of the process stream by controlling an amount of biocide(s) added to the process stream, a selection of points of addition of biocide(s), or selection of a type of biocide(s) or any combination thereof.

9. The method according claim 1, which further includes identifying process streams to be monitored and/or locations of these process streams to be monitored.

10. An online device for monitoring a microbiological state of a process stream of an industrial process by measuring concentration of dissolved oxygen and determining a rH value, in said stream, wherein the rH value is determined by measuring a pH and a redox potential of a sample of the process stream and by calculating the rH value by adding the measured pH and redox potential of the sample together, modified by constants, the device comprising
  a measuring unit with an inlet and an outlet for holding the sample to be measured, and within said measuring unit:
    means for carrying out initial measurements of the concentration of dissolved oxygen and the rH value at the beginning of the measurement of the concentration of dissolved oxygen and the determination of the rH value, to determine whether process stream has aerobic or anaerobic conditions;
    means for measuring, at two or more time points, the concentration of dissolved oxygen in the sample to calculate relative dissolved oxygen consumption if the process stream has aerobic conditions between the two of said two or more time points; and means for determining at least at two time points, which may be the same or different than the two or more time points for measuring the concentration of dissolved oxygen, the rH value of the sample in order to calculate at least one of change of the rH value and relative change of the rH value if the process stream has anaerobic conditions between said at least two time points;

means for determining the microbiological state of the process stream based on at least the rH value, the change of the rH value and the relative change of the rH value if the process stream has anaerobic conditions, and means for determining the microbiological state of the process stream, based on relative dissolved oxygen consumption and optionally based on the rH value if the process stream has aerobic conditions, means for correlating the relative dissolved oxygen consumption and optionally the rH value to the amount of aerobic bacteria in the process stream, and means for correlating one or more of the rH value, the change of the rH value and the relative change of the rH value to the amount of anaerobic bacteria in the process stream; and means for controlling the microbiological state of the process stream by adding an amount of biocide(s) to the process stream based on results of the correlating the relative dissolved oxygen consumption and optionally the rH value to the amount of aerobic bacteria in the process stream, and correlating one or more of the rH value, the change of the rH value and the relative change of the rH value to the amount of anaerobic bacteria in the process stream.

11. The device according to claim 10, further comprising an inlet conduit for directing a sample to the measuring unit and an outlet conduit for directing the sample away from the measuring unit, the inlet conduit being in connection with a main process line, whereby the inlet conduit allows taking a side-draw from the main process line.

12. The device according to claim 10, further comprising means for measuring a temperature and a pressure sensor.

13. The device according to claim 10, further comprising means for controlling and monitoring a function of the device.

14. The device according to claim 10, further comprising means for calculating an amount of biocide to be added into the process line and means for dosing said biocide into the process line.

15. The method according to claim 1, wherein the process stream has aerobic conditions if rH >23.

16. The method according to claim 1, wherein the process stream has anaerobic conditions if rH is 0-15.

* * * * *